(12) United States Patent
Lin et al.

(10) Patent No.: US 7,611,844 B2
(45) Date of Patent: Nov. 3, 2009

(54) METHODS FOR DETECTING ASYMMETRIC DIMETHYLARGININE IN A BIOLOGICAL SAMPLE

(75) Inventors: Ken Y. Lin, Boston, MA (US); John Cooke, Palo Alto, CA (US)

(73) Assignee: Board of Trustees of the Leland Stanford Jr. University, Palo Alto, CA (US)

( * ) Notice: Subject to any disclaimer, the term of this patent is extended or adjusted under 35 U.S.C. 154(b) by 68 days.

(21) Appl. No.: 10/713,674

(22) Filed: Nov. 13, 2003

(65) Prior Publication Data

US 2004/0214252 A1 Oct. 28, 2004

Related U.S. Application Data

(60) Provisional application No. 60/426,677, filed on Nov. 15, 2002.

(51) Int. Cl.
*G01N 33/53* (2006.01)
*G01N 33/543* (2006.01)
(52) U.S. Cl. .................. 435/7.1; 436/161; 436/172; 436/175; 436/177; 436/178; 436/518
(58) Field of Classification Search .............. 435/4, 435/7.1, 7.92, 7.93, 114, 962; 436/69, 71, 436/111, 112, 825, 175, 177, 161; 210/668, 210/690–692, 719, 749; 562/560; 260/998.22; 424/175.1, 140.1, 194.1, 195.11, 279.1
See application file for complete search history.

(56) References Cited

U.S. PATENT DOCUMENTS

| 5,318,680 | A * | 6/1994 | Fishman et al. .............. 204/453 |
| 6,358,699 | B1 | 3/2002 | Balint et al. |
| 6,699,673 | B2 | 3/2004 | Aletta |
| 6,720,188 | B2 | 4/2004 | Kaddurah-Daouk et al. |
| 6,736,957 | B1 * | 5/2004 | Forrow et al. ............... 205/777.5 |
| 2006/0201805 | A1 * | 9/2006 | Forrow et al. ............... 204/403.1 |

FOREIGN PATENT DOCUMENTS

WO WO 98/49199 * 11/1998

OTHER PUBLICATIONS

Duerksen PJ & Wilkinson KD. Immobilization of proteins via arginine residues. Anal. Biochem. 1987;160:444-454.*
Schwarzenbolz, U. et al. On the reaction of glyoxal with proteins. Z. Lebensm. Unters Forsch. A. 1997;205:121-124.*
Sopio, R. & Lederer, M. Reaction of 3-deoxypentosulose with N-methyl- and N,N-dimethylguanidine as model reagents for protein-bound arginine and for creatine. Z. Lebensm. Unters Forsch. A. 1995;201:381-386.*
Baburaj, K. et al. HOCGO and DMACGO. Two coumarin derived a-dicarbonyls suitable as pH and polarity sensitive fluorescent reporters for proteins that can be targeted at reactive arginines. Biochim. Biophys. Acta. 1994;1199:253-265.*
Ogawa et al. Metabolism of N,N- and N,N'-dimethylarginine in rats. Arch. Biochem. Biophys. 1987;252:526-537.*
Cooper, A.J.L. & Meister, A. Cyclic forms of the alpha-keto acid analogs of arginine, citrulline, homoarginine, and homocitrulline. J. Biol. Chem. 1978;253:5407-5410.*
Takahashi (1968) *J. Biol. Chem.* 243:6171-6179.
Stühlinger et al. (2002) *J. Am. Med. Assoc.* 287:1420-1426.
Teerlink et al. (2002) *Anal. Biochem.* 303:131-137.
Dobashi et al. (2002) *Analyst* 127:54-59.
Vishwanathan et al. (2000) *J. Chromatogr. B. Biomed. Sci. Appl.* 748:157-166.
Pi et al. (2000) *J. Chromatogr. B. Biomed. Sci. Appl.* 742:199-203.
Chen et al. (1997) *J. Chromatogr. B. Biomed. Sci. Appl.* 692:467-471.
Pettersson et al. (1997) *J. Chromatogr. B. Biomed. Sci. Appl.* 692:257-262.
Bode-Boger, S.M. et al., Elevated L-arginine/dimethylarginine ratio contributes to enhanced systemic NO production by dietary L-arginine in hypercholesterolemic rabbits. Biochem. Biophys. Res. Commun. Feb. 1996, vol. 219, pp. 598-603.

* cited by examiner

*Primary Examiner*—Christopher L Chin
(74) *Attorney, Agent, or Firm*—Paula A. Borden; Bozicevic, Field & Francis LLP

(57) ABSTRACT

The present invention provides methods of detecting asymmetric dimethylarginine (ADMA) in a sample, particularly a sample that may contain symmetrical dimethylarginine (SDMA) and/or arginine. The methods generally involve modifying any SDMA and arginine in the sample such that SDMA and arginine are readily distinguishable from ADMA; and detecting ADMA. The invention further provides antibodies specific for ADMA; antibodies specific for modified SDMA; and antibodies specific for modified arginine. The invention further provides kits for practicing the subject methods.

16 Claims, 4 Drawing Sheets

NBD-F labeled ADMA

METHODS FOR DETECTING ASYMMETRIC DIMETHYLARGININE IN A BIOLOGICAL SAMPLE

CROSS-REFERENCE

This application claims the benefit of U.S. Provisional Patent Application No. 60/426,677 filed Nov. 15, 2002, which application is incorporated herein by reference in its entirety.

STATEMENT REGARDING FEDERALLY SPONSORED RESEARCH

The U.S. government may have certain rights in this invention, pursuant to grant no. R01 HL-63685 awarded by the National Institutes of Health, the National Heart, Lung and Blood Institute.

FIELD OF THE INVENTION

The present invention is in the field of assay methods, and in particular assay methods for asymmetric dimethylarginine.

BACKGROUND OF THE INVENTION

Elevated asymmetric dimethylarginine (ADMA) levels have been observed in various conditions, including hypertension, dyslipidemia, hyperglycemia, hyperhomocysteinemia, and renal failure, and are believed to be one cause of endothelial dysfunction in these conditions. Elevated plasma ADMA concentrations are also associated with an increased risk of cardiovascular disease. As an endogenous inhibitor of nitric oxide synthase, ADMA reduces nitric oxide (NO) production. NO plays a vital part in the vascular homeostasis. Aside from being the most potent vasodilator, NO inhibits platelet aggregation, smooth muscle proliferation, and adhesion molecule expression, which all play a part in atherogenesis. Throughout the last few years, basic scientific investigation has revealed the mechanism whereby ADMA becomes elevated in patients with hypertension, hyperhomocysteinemia, hyperglycemia, hypercholesterolemia, and tobacco exposure.

Nevertheless, the field of ADMA is progressing slowly, mostly because of the laborious procedures required to quantify the molecule. A conclusive demonstration of ADMA's clinical relevance requires clinical studies with a great patient population. High pressure liquid chromatography (HPLC) is the most commonly used method to quantify ADMA. However, the use of HPLC to quantitate ADMA suffers from several drawbacks. The most critical among them are efficiency and sensitivity. The labor-intensive extraction and derivatization steps necessary for HPLC detection not only makes the procedure more vulnerable to human errors, but also makes it unfitting for studies with a large sample size. Moreover, because the detection limit for UV detectors seldom goes below the sub-micromolar level, intracellular ADMA level in disease states remains largely unexplored, despite the fact that ADMA is generated intracellularly.

There is a need in the art for methods of detecting and quantitating ADMA that are simple, efficient, and readily adapted to high-throughput analysis. The present invention addresses this need.

Literature

Takahashi (1968) *J. Biol. Chem.* 243:6171-6179; Stühlinger et al. (2002) *J. Am. Med. Assoc.* 287:1420-1426; U.S. Pat. No. 6,358,699; Teerlink et al. (2002) *Anal. Biochem.* 303:131-137; Dobashi et al. (2002) *Analyst* 127:54-59; Vishwanathan et al. (2000) *J. Chromatogr. B. Biomed. Sci. Appl.* 748:157-166; Pi et al. (2000) *J. Chromatogr. B. Biomed. Sci. Appl.* 742:199-203; Chen et al. (1997) *J. Chromatogr. B. Biomed. Sci. Appl.* 692:467-471; Pettersson et al. (1997) *J. Chromatogr. B. Biomed. Sci. Appl.* 692:257-262.

SUMMARY OF THE INVENTION

The present invention provides methods of detecting asymmetric dimethylarginine (ADMA) in a sample, particularly a sample that may contain symmetrical dimethylarginine (SDMA) and/or arginine. The methods generally involve modifying any SDMA and arginine in the sample such that SDMA and arginine are readily distinguishable from ADMA; and detecting ADMA. The invention further provides antibodies specific for ADMA; antibodies specific for modified SDMA; and antibodies specific for modified arginine. The invention further provides kits for practicing the subject methods.

FEATURES OF THE INVENTION

The present invention features a method of detecting asymmetric dimethylarginine (ADMA) in a sample comprising ADMA, symmetric dimethylarginine (SDMA), and arginine. The method generally involves: a) contacting a sample with an α-dicarbonyl compound, wherein said sample is suspected of containing ADMA and at least one of SDMA and arginine, where the contacting step results in modification of the guanidino nitrogens of SDMA and the guanidino nitrogens of arginine, to produce modified SDMA and modified arginine; and b) detecting ADMA in the sample. In some embodiments, the α-dicarbonyl compound is phenylglyoxal.

In some embodiments, the method further involves the step of modifying the α-amino group of SDMA, ADMA, and arginine before the step of modifying the guanidino nitrogens of SDMA and the guanidino nitrogens of arginine. In some of these embodiments, the α-amino group is modified with a dye that provides a detectable signal.

In some embodiments, the detection step involves contacting the sample with an antibody that binds specifically to dimethylarginines, wherein the antibody does not bind to the modified SDMA. In other embodiments, the detection step involves contacting the sample with an antibody that binds specifically to ADMA. In some of these embodiments, the antibody is detectably labeled.

In some embodiments, detection of ADMA is by high performance liquid chromatography. In other embodiments, detection of ADMA is by capillary electrophoresis.

The present invention further features an antibody that binds specifically to asymmetric dimethylarginine. In some embodiments, the antibody is detectably labeled.

The present invention further features an antibody that binds specifically to modified symmetric dimethylarginine (SDMA), wherein the guanidino nitrogens of the SDMA are modified by reaction with an α-dicarbonyl compound.

The present invention further features a kit for detecting asymmetric dimethylarginine (ADMA) in a sample. In some embodiments, the kit includes an α-dicarbonyl agent that modifies the guanidino nitrogens of SDMA and the guanidino nitrogens of arginine; and an antibody that binds to ADMA. In other embodiments, the kit further includes an antibody that binds α-dicarbonyl-modified SDMA, and an antibody that binds α-dicarbonyl-modified L-arginine.

DEFINITIONS

Figure 1:
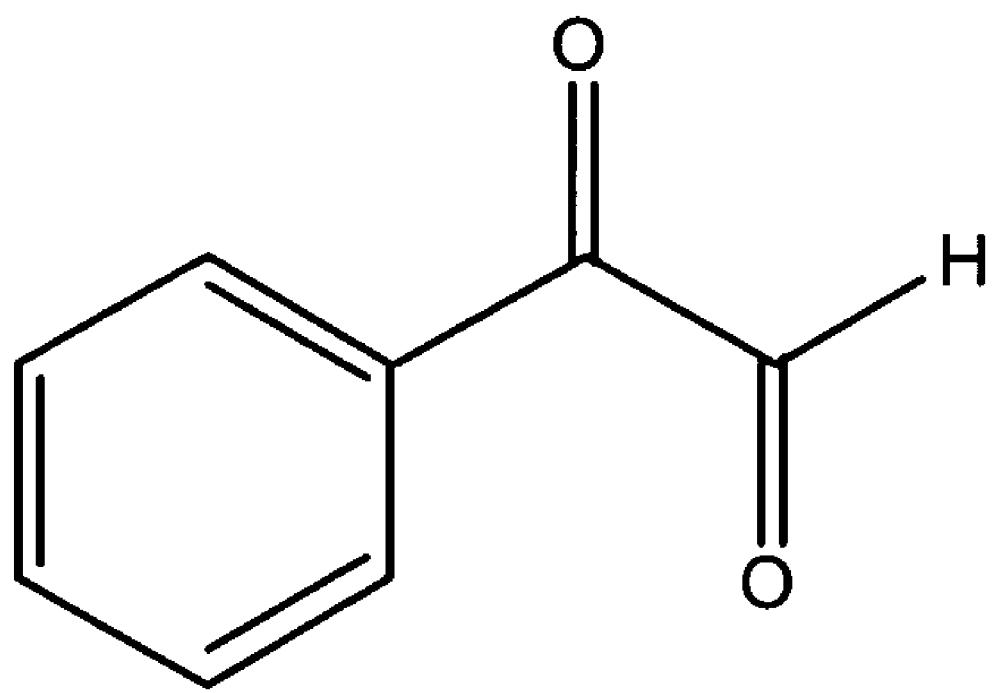
FIG. 1 depicts the structure of phenylglyoxal.

Assay methods of the invention may be qualitative or quantitative. Thus, as used herein, the term "detection" refers to both qualitative and quantitative determinations, and therefore includes "measuring" and "determining a level of."

A "biological sample" encompasses a variety of sample types obtained from an individual and can be used in a diagnostic or monitoring assay. The definition encompasses blood, blood-derived samples, and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components. The term "biological sample" encompasses a clinical sample, and also includes cells in culture, cell supernatants, cell lysates, serum, plasma, cerebrospinal fluid, urine, saliva, biological fluid, and tissue samples.

The term "binds specifically," in the context of antibody binding, refers to high avidity and/or high affinity binding of an antibody to a specific molecule, e.g., asymmetric dimethylarginine (ADMA), modified symmetric dimethylarginine (SDMA), or modified arginine. For example, binding of an ADMA-specific antibody to ADMA is stronger than binding of the same antibody to arginine, SDMA, or modified SDMA, so that by adjusting binding conditions, the antibody binds almost exclusively to ADMA and not to arginine, SDMA, modified arginine, or modified SDMA. Likewise, binding of an antibody specific to modified SDMA is stronger than binding of the same antibody to arginine, ADMA, modified ADMA, or SDMA, so that by adjusting binding conditions, the antibody binds almost exclusively to SDMA and not to arginine, ADMA, modified ADMA, or SDMA.

Antibodies which bind specifically to ADMA, to modified SDMA, or to modified arginine may be capable of binding other molecules at a weak, yet detectable, level (e.g., 10% or less of the binding shown to ADMA, modified SDMA, or modified arginine). Such weak binding, or background binding, is readily discernible from the specific antibody binding to ADMA, modified SDMA, or modified arginine, e.g. by use of appropriate controls. In general, antibodies of the invention which bind to ADMA, modified SDMA, or modified arginine, with a binding affinity of $10^{-7}$ mole/l or more, e.g., $10^{-8}$ mole/liters or more (e.g., $10^{-9}$ M, $10^{-10}$, $10^{-11}$, etc.) are said to bind specifically to ADMA, modified SDMA, or modified arginine, respectively. In general, an antibody with a binding affinity of $10^{-6}$ mole/liters or less is not useful in that it will not bind an antigen at a detectable level using conventional methodology currently used.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an α-dicarbonyl compound" includes a plurality of such compounds and reference to "the modified SDMA" includes reference to one or more modified SDMA molecules and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of detecting asymmetric dimethylarginine (ADMA) in a sample, particularly in a sample that may contain SDMA and/or arginine. The methods generally involve modifying symmetrical dimethylarginine (SDMA) and arginine such that SDMA and arginine are readily distinguishable from ADMA; and detecting ADMA. The invention further provides antibodies specific for ADMA, antibodies specific for modified SDMA, and antibodies specific for modified arginine. The invention further provides kits for practicing the subject methods.

Methods of Detecting ADMA in a Biological Sample

The present invention provides methods of detecting ADMA in a biological sample, particularly in a sample that may contain SDMA and/or arginine. The biological sample may comprise ADMA, SDMA, and arginine. The methods involve modifying SDMA and arginine in such a way that the modified SDMA and modified arginine are readily distinguishable from ADMA. The methods involve contacting a biological sample with an α-dicarbonyl compound, generating modified SDMA and modified arginine; and detecting ADMA in the sample.

The structures of arginine, ADMA, and SDMA are shown below. The instant methods involve modifying the guanidino nitrogen groups of SDMA and of arginine with an α-dicarbonyl compound. SDMA and arginine are modified with the α-dicarbonyl compound, while ADMA is not.

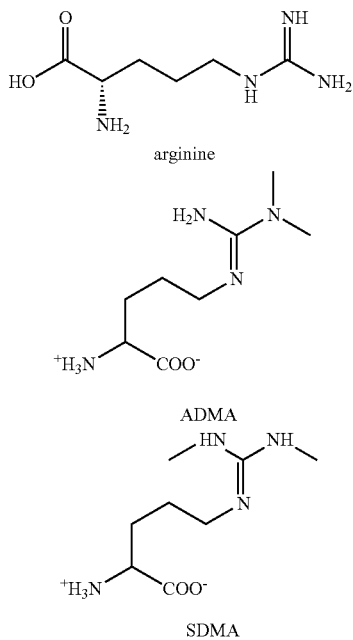

Acting as nucleophiles, the guanidino nitrogens of arginine attack the carbonyl carbons of the α-dicarbonyl compound, generating a modified arginine that contains two modified nitrogen groups per guanidino group. Since the guanidino nitrogens on SDMA each take up one methyl group, they both still possess a hydrogen that is free to participate in a nucleophilic reaction. Thus, as with arginine, the guanidino nitrogens of SDMA are also modified by the α-dicarbonyl compound to form a stable product. Without wishing to be bound by theory, it is believed that participation of both guanidino nitrogens with the α-dicarbonyl compound is crucial for modification of the compound because the resultant 5-membered ring structure stabilizes the intermediate product. Because ADMA has both methyl groups occupying the same guanidino nitrogen, the guanidino nitrogen is not available for reacting with the α-dicarbonyl compound, and ADMA does not react with an α-dicarbonyl compound to form a stable product.

Modifying SDMA and Arginine

Any of a variety of α-dicarbonyl compounds that are known in the art can be used in the instant methods to modify guanidino nitrogens of SDMA and arginine. The structure of a generic α-dicarbonyl compound is shown below.

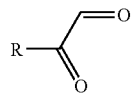

Suitable α-dicarbonyl compounds include, but are not limited to, dialdehydes, ketoaldehydes, and diketones. Non-limiting examples of α-dicarbonyl compounds are biacetyl, pyruvic acid, glyoxal, methyglyoxal, deoxyosones, 3-deoxyosones, malondialdehyde, 2-oxopropanal, phenylglyoxal, 2,3-butanedione, and 1,2-cyclohexanedione.

In many embodiments, R is a bulky group, including, but not limited to, a cyclopentyl group, a substituted cyclopentyl group; a six-membered ring, such as phenyl, a substituted phenyl (e.g., p-hydroxyphenylglyoxal, nitrophenylglyoxal, etc.), and the like. In embodiments of particular interest, the α-dicarbonyl compound is phenylglyoxal. The structure of phenylglyoxal is shown below.

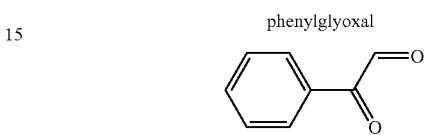

As one non-limiting example, where the α-dicarbonyl compound is phenylglyoxal, the reaction with arginine proceeds as follows:

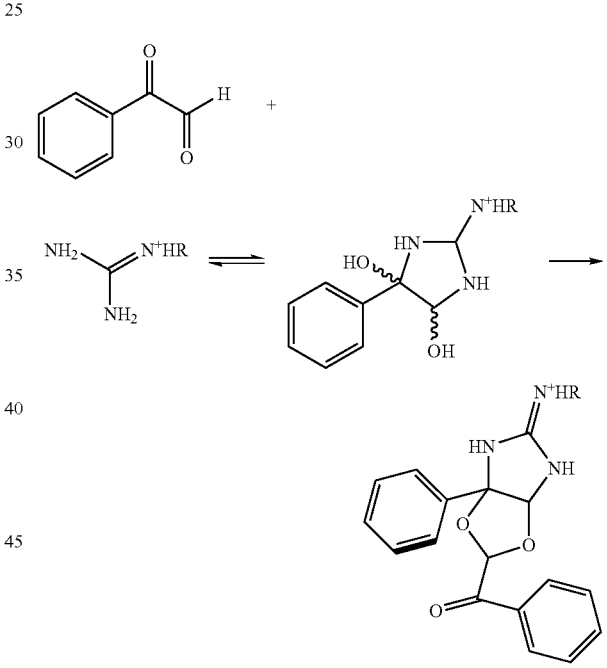

The reaction with SDMA proceeds in a similar way.

In addition to reacting with the guanidino amine of arginine, phenylglyoxal has been reported to react with the α-amino group of the peptides to give α-keto acyl peptides. Takahashi (1968) *J. Biol. Chem.* 243:6171-6179. In the context of free amino acid, this observation indicates that phenylglyoxal will react with all α-amino groups of all amino acid. In some embodiments, the α-amino group is protected with a conventional labeling dye such as fluoro-nitro-benzoxadiazole (NBD-F), as described further below. Protection of the α-amino group ensures that phenylglyoxal only reacts with the guanidino nitrogen. Many labeling dye molecules are conjugated to the amino acid or proteins by reacting with the α-amino group.

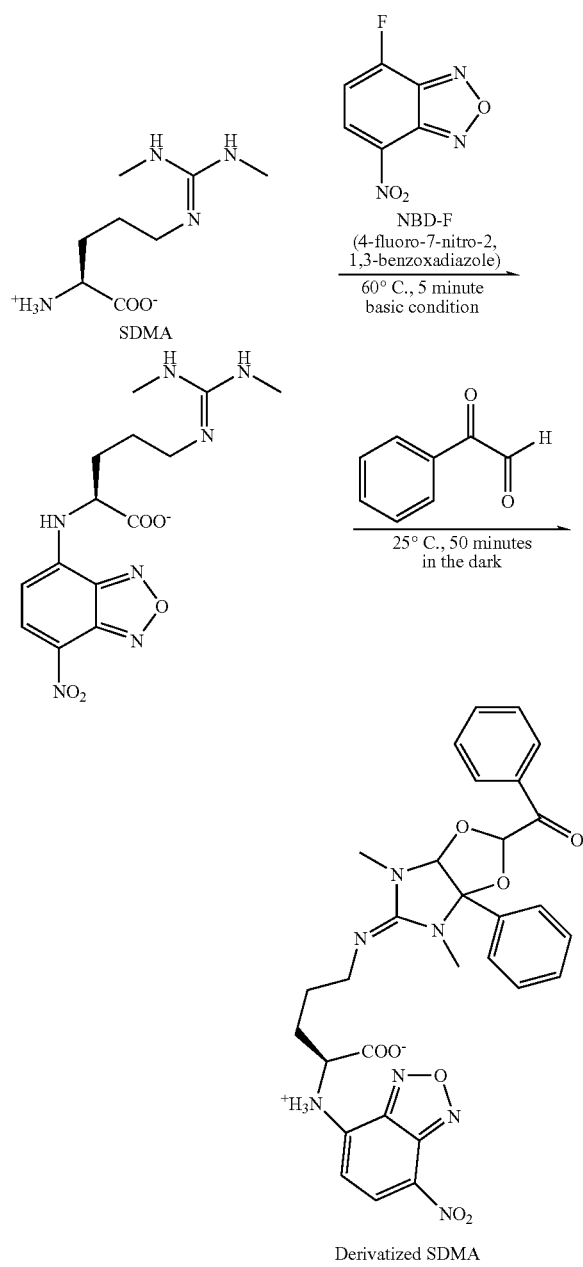

Derivatized SDMA

An α-dicarbonyl compound is contacted with a biological sample. Generally, the α-dicarbonyl compound is prepared in water, and the pH of the solution is adjusted to 9.0 with 1M NaOH. The α-dicarbonyl compound is generally in a 10× stock solution in a concentration of from about 1 mM to about 500 mM, e.g., from about 1 mM to about 10 mM, from about 10 mM to about 50 mM, from about 50 mM to about 100 mM, from about 100 mM to about 200 mM, from about 200 mM to about 300 mM, from about 300 mM to about 400 mM, or from about 400 mM to about 500 mM. In some embodiments, the α-dicarbonyl compound is in a 10× stock solution in a concentration of from about 50 mM to about 100 mM. A solution containing the α-dicarbonyl compound is added to the biological sample in such a way that the stock solution is diluted 10-fold.

The biological sample is contacted with the α-dicarbonyl compound, and the reaction is allowed to proceed for a period of time of from about 15 seconds to 2 hours, e.g., from about 15 seconds to about 60 seconds, from about 1 minute to about 15 minutes, from about 15 minutes to about 30 minutes, from about 30 minutes to about 60 minutes, or from about 1 hour to about 2 hours. In a particular embodiment, the reaction is allowed to proceed for 1 hour to about 2 hours in the dark at room temperature (e.g., at about 22° C.).

The reaction of components in the sample with the α-dicarbonyl compound results in modification of the guanidino nitrogen groups of substantially all molecules of SDMA and arginine in the sample. Thus, at least 80%, at least 90%, at least 95%, at least 98%, or at least 99% of the SDMA and arginine molecules in the sample are modified.

A variety of other reagents may be included in the assay. These include reagents such as buffers, salts, neutral proteins, e.g. albumin, detergents, etc. Reagents that improve the efficiency of the assay, such as protease inhibitors, nuclease inhibitors, anti-microbial agents, etc. may also be used.

The instant assay methods may be designed a number of different ways. For example, the assay components of the method may be combined at substantially the same time or at different times. Incubations are performed at any suitable temperature, typically between 4° and 40° C. Incubation periods are selected for optimum activity, but may also be optimized to facilitate rapid high-throughput screening. In general, all components are in solution.

An example of a biological sample is serum. However, any biological sample can be used. As one non-limiting example, serum or plasma is obtained from a blood sample of a patient, and from about 0.05 mL to about 2.0 mL of serum or plasma is reacted with an α-dicarbonyl compound such that the final concentration of the α-dicarbonyl compound in the sample is in a range of from about 30 mM to about 70 mM. The reaction is allowed to proceed for a suitable time, after which ADMA is detected.

Protecting the α-Amino Group

The α-dicarbonyl compound may react with the α-amino group of arginine, SDMA, and ADMA. In such cases, an optional step of derivatizing the α-amino group of arginine, SDMA, and ADMA is performed before the modification of the guanidino nitrogen groups of arginine and SDMA. Many methods are known in the art for modifying (protecting) the α-amino group.

Protecting groups for α-amino groups are well known in the art include, but are not limited to, methyl, formyl, ethyl, acetyl, t-butyl, anisyl, benzyl, trifluoroacetyl, N-hydroxysuccinimide, t-Butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulphenyl, 4-toluenesulfphonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, 2,2,5,7,8-pentamethyl-chroman-6-sulphonyl, 2-(4-nitrophenyl sulfonyl)ethoxy carbonyl, 9-(2-sulfo)fluorenylmethyl carbamate, 9-(2,7-dibromo)fluorenylmethyl carbamate, 17-tetrabenzol[a,c,g,i]fluorenyl methyl carbamate, 1,1-dioxobenzol[b]thiophen-2-ylmethyl carbamate, and the like.

Also suitable for use are groups that both protect the α-amino group and provide for detection, e.g., the protecting group is a detectable label. Suitable fluorophores for this invention include fluorescein and its analogs, rhodamine and its analogs, cyanine and related polymethines and their analogs, and the like. Specific fluorophores which are suitable for use with the present invention are Fluorescein isothiocyanate (FITC); 4-fluoro-7-nitrobenzofurazan (NBD-F); Texas Red™ (Molecular Probes, Inc.; Eugene, Oreg.); tetramethyl rhodamine isothiocyanate (TRITC); and Cyanine dyes, e.g., Cy3, Cy5, Cy5.5 Cy7, Cy7.5, Cy8 and Cy9 (Biological Detection Systems, Pittsburgh, Pa.); phenyl-thiohydantoin (PTH), and phenylisothiocyanate (PITC). As one non-limiting example (see above), the α-amino group is reacted with 4-fluoro-7-nitro-benzoxadiazole (NBD-F).

Detecting ADMA

ADMA is detected using any of a variety of methods. Such methods include, but are not limited to, conversion of ADMA to citrulline, followed by spectrophotometric determination of citrulline; determination of ADMA with an antibody that binds dimethylarginines; determination of ADMA with an antibody specific for ADMA, using an immunological assay; high performance liquid chromatography; capillary electrophoresis; and the like. Detection of ADMA can be qualitative or quantitative. These methods are also useful for detecting derivatized SDMA and L-arginine, which, after reacting as described above, are more easily distinguished from ADMA. Various methods are outlined below.

HPLC Methods

A variety of methods for detecting ADMA using HPLC are known in the art, any of which can be used in conjunction with an instant assay method. See, e.g., Teerlink et al. (2002) *Anal. Biochem.* 303:131-137; Dobashi et al. (2002) *Analyst* 127: 54-59; Pi et al. (2000) *J. Chromatogr. B. Biomed. Sci. Appl.* 742:199-203; Chen et al. (1997) *J. Chromatogr. B. Biomed. Sci. Appl.* 692:467-471; Anderstam et al. (1997) *J. Am. Soc. Nephrol.* 8:1487-1442; and Pettersson et al. (1997) *J. Chromatogr. B. Biomed. Sci. Appl.* 692:257-262.

Where HPLC is used to detect ADMA in a sample, the α-amino group of ADMA is modified (derivatized) with a detectable group, e.g., a fluorescent group. After the α-amino group is derivatized, the sample is treated with an α-dicarbonyl compound as described above. This will cause SDMA and arginine, but not ADMA, to be modified, so as to enhance their separation from ADMA when the sample is applied to an HPLC column. Separation of analytes is performed on the HPLC using a solvent. The analytes, including ADMA, are eluted, and the amount of ADMA is determined by measuring the amount of the detectable label in each analyte peak. The amount of ADMA can be determined by determining the peak area.

Solid phase extraction (SPE) of the biological sample is frequently carried out to clean up the sample prior to applying the sample to the HPLC column. A variety of SPE columns are available and can be used in conjunction with the instant methods. Suitable SPE columns include an Oasis MCX SPE column (Waters); a Bond Elute SCX 50 mg column (Varian Inc., Palo Alto, Calif.); and the like. These columns retain positively-charged compounds, which are then collected by eluting the column with a weak base such as trimethylamine.

The following is one non-limiting example of a method of detecting ADMA using HPLC. In this method, the biological sample is cleaned up on an SPE column; the primary amine containing compounds (eg. ADMA, SDMA, arginine) are derivatized with an ortho-phthaldialdehyde reagent containing 3-mercaptopropionic acid; and, after this derivatization, the sample is treated with an α-dicarbonyl compound and then the derivatized sample is applied to a reversed-phase HPLC, and the peak corresponding to ADMA is detected with fluorescence detection. The peak corresponding to ADMA is clearly distinguished from peaks corresponding to L-arginine or SDMA.

In this example, the biological sample is first cleaned up on a SPE column. 0.2 ml of biological sample (e.g., plasma, serum, urine, cerebrospinal fluid, and the like) is mixed with 0.1 ml of an internal standard and 0.7 ml phosphate buffered saline. The sample is applied to an Oasis MCX SPE column (Waters). After application of the sample, the column is washed consecutively with 1.0 ml of 100 mM HCl and 1.0 ml methanol. Analytes are eluted from the column in 3.0-ml tubes with 1.0 ml concentrated ammonia (or triethylamine)/water/methanol (10/40/50). The solvent is removed from the analytes by evaporation with nitrogen at a temperature of 60-80° C. The residue is dissolved in 0.1 ml water to form the analyte sample.

In this example, analytes eluted from the SPE column are derivatized with ortho-phthaldialdehyde (OPA). To the 0.1 ml analyte sample is added 0.1 ml OPA working solution. OPA stock solution is prepared by dissolving 10 mg OPA in 0.2 ml methanol, followed by addition of 1.8 ml of a 200 mM potassium borate buffer (pH 9.5) and 10 μl 3-mercaptopropionic acid. The OPA working solution is prepared by five-fold dilution of the stock solution with borate buffer. The final concentrations of OPA and 3-mercaptopropionic acid in the working OPA solution are 7.5 mM and 11.5 mM, respectively. After the OPA working solution is added to the analyte sample, the samples are derivatized with an α-dicarbonyl compound, and are applied to an HPLC column.

In this example, HPLC is performed on a Symmetry C18 column (3.9×150 mm; 5 μm particle size; 100 Å pore size) with a 10×3 mm guard column packed with the same stationary phase. Mobile phase A consists of 50 mM potassium phosphate buffer (pH 6.5), containing 8.7% acetonitrile, and mobile phase B is acetonitrile/water (50/50, v/v). Separation is performed under isocratic conditions with 100% mobile phase A at a flow rate of 1.1 muminute and a column temperature of 30° C. After elution of the last analyte, closely related compounds are eluted with a strong solvent flush (50% B from 20 to 22 minutes). Fluorescence is measured at excitation and emission wavelengths of 340 an 455 nm, respectively. Peaks are quantified on the basis of peak area.

Those skilled in the art will recognize that many modifications to the above example of an HPLC method are possible.

Capillary Electrophoresis

Where CE is used to detect ADMA content of a sample, α-amino groups of all of the amino acids (including that of ADMA) are modified with a labeling group (e.g., NBD-F). Subsequently, SDMA and L-arginine are derivatized with an α-dicarbonyl compound.

Methods of using capillary electrophoresis to detect ADMA are known in the art, and any known method can be used in conjunction with the instant methods. See, e.g., Vallance et al. (1992) *Lancet* 339:572-575; and Causse et al. (2000) *J. Chromatogr. B. Biomed. Sci. Appl.* 741:77-83.

Immunoassays

A variety of immunoassays can be designed that make use of the ability to distinguish modified SDMA and modified arginine from ADMA. In carrying out an immunoassay, one or more of the following antibodies will be used: (1) antibodies that bind dimethylarginines, i.e., that specifically bind both SDMA and ADMA and that do not discriminate between SDMA and ADMA; (2) antibodies that specifically bind ADMA; (3) antibodies that specifically bind modified SDMA; (4) antibodies that bind both modified SDMA and modified L-arginine; and (5) antibodies that specifically bind modified arginine.

Modification of arginine and SDMA as described above modifies these molecules such that they no longer react with antibodies that bind both SDMA and ADMA (i.e., antibodies specific for dimethylarginines). Thus, in some embodiments, determination of ADMA following modification of arginine and SDMA is carried out with conventional immunological assays, using antibodies specific for dimethylarginines. Because substantially all of the SDMA in the sample is modified by the α-dicarbonyl compound during the modification reaction, and because the modified SDMA is not recognized by antibodies specific for dimethylarginines, such antibodies will only detect ADMA in the sample.

Detection of ADMA can also be carried out using an antibody specific for ADMA (e.g., antibody that binds ADMA, but that does not substantially bind to SDMA, arginine, or modified SDMA), as described in more detail below.

Immunoassays can also be carried out using antibodies specific for modified SDMA and antibodies specific for modified arginine, as described in more detail below.

Detection with a specific antibody is carried out using well-known methods. In general, the antibody is detectably labeled, either directly or indirectly. Direct labels include radioisotopes (e.g., $^{125}$I; $^{35}$S, and the like); enzymes whose products are detectable (e.g., luciferase, β-galactosidase, horse radish peroxidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Fluorescent proteins include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from *Anthozoan* species, as described in, e.g., Matz et al. (1999) *Nature Biotechnol.* 17:969-973; and the like.

Indirect labels include second antibodies that bind to antibodies specific for ADMA or dimethylarginines, wherein the second antibody is labeled as described above. Indirect labels also include members of specific binding pairs, e.g., biotin-avidin, and the like, as are well known in the art. For example, the primary antibody may be conjugated to biotin, with horseradish peroxidase-conjugated avidin added as a second stage reagent. Final detection uses a substrate that undergoes a color change in the presence of the peroxidase. Alternatively, the secondary antibody conjugated to a fluorescent compound, e.g. fluorescein, rhodamine, Texas red, etc. The absence or presence of antibody binding may be determined by various methods, including spectrophotometric detection, fluorimetry, radiography, scintillation counting, etc.

Quantification can be carried out using any known method, including, but not limited to, enzyme-linked immunosorbent assay (ELISA); radioimmunoassay (RIA); and the like. In general, quantitation is accomplished by comparing the level of ADMA detected in the sample with the amount of ADMA present in a standard curve.

In many embodiments, an assay will employ a specific antibody (e.g., an antibody specific for ADMA, or an antibody specific for dimethylarginines), which antibody is bound to a solid support, such as a test strip. Test strips are in provided in a variety of shapes (e.g., rectangles, squares, circles, etc.) and materials (e.g. nylon, polyvinyl pyrollidone, polyester, polycarbonate, cellulose acetate, polyethersulfone, nitrocellulose, and the like). Such assays can be designed in any of a number of ways. In general, a specific antibody is bound to a test strip, and the antibody bound to the test strip captures ADMA in the sample. For example, a sample is applied to one end of a test strip, and the components of the sample are allowed to migrate by capillary action or lateral flow. Methods and devices for lateral flow separation, detection, and quantitation are known in the art. See, e.g., U.S. Pat. Nos. 5,569,608; 6,297,020; and 6,403,383. Once the ADMA is captured by the bound antibody, a second antibody that is detectably labeled is used to detect the captured ADMA.

In another embodiment, a sample that has been modified as described above is spotted onto a membrane (e.g., nylon, polyvinyl pyrollidone, polyester, polycarbonate, cellulose acetate, polyethersulfone, nitrocellulose, and the like). Typically, several spots that correspond to increasing dilutions of the sample are applied. For example, serial 1:2 dilutions are made and spotted onto the membrane. Detectably labeled antibody specific for ADMA or detectably labeled antibody specific for dimethylarginines is used to quantitate the level of ADMA in the sample.

In other embodiments, an assay will employ an antibody specific for modified SDMA, which antibody is bound to a solid support. For example, a test strip is used that includes, in order from a first end to a second end, a sample loading region, a first antibody region that includes an antibody specific for modified SDMA, and a second region that includes an antibody that binds ADMA (either an antibody specific for ADMA or an antibody specific for dimethylarginines). A sample is applied to the sample loading region, and the components of the sample are allowed to migrate toward the second end of the test strip by capillary action or lateral flow. Modified SDMA is captured in the first region, leaving ADMA free to migrate to the second region, where it is captured. The captured ADMA is detected as described above.

In other embodiments, an assay will employ an antibody specific for modified SDMA and an antibody specific for modified arginine, which antibodies are bound to a solid support. For example, a test strip is used that includes, in order from a first end to a second end, a sample loading region, a first antibody region that includes an antibody specific for modified SDMA, a second region that includes an antibody that binds modified arginine, and a third region that includes an antibody that binds ADMA (either an antibody specific for ADMA or an antibody specific for dimethylarginines). A sample is applied to the sample loading region, and the components of the sample are allowed to migrate toward the second end of the test strip by capillary action or lateral flow. Modified SDMA is captured in the first region, modified arginine is captured in the second region, leaving ADMA free to migrate to the third region, where it is captured. The captured ADMA is detected as described above.

As an alternative, the antibody specific for modified SDMA and modified arginine can be combined into a first region. For example, a test strip is used that includes, in order from a first end to a second end, a sample loading region, a first antibody region that includes an antibody specific for modified SDMA and an antibody that binds modified arginine; and a second region that includes an antibody that binds ADMA (either an antibody specific for ADMA or an antibody specific for dimethylarginines). A sample is applied to the sample loading region, and the components of the sample are allowed to migrate toward the second end of the test strip by capillary action or lateral flow. Modified SDMA and modified arginine are captured in the first region, leaving ADMA free to migrate to the second region, where it is captured. The captured ADMA is detected as described above.

Other Assays

Other methods of detecting ADMA include liquid chromatography-tandem mass spectrometry. See, e.g., Vishwanathan et al. (2000) *J. Chromatogr. B. Biomed. Sci. Appl.* 748:157-166.

Assays for detecting ADMA can also be carried out on a sample that is depleted of modified SDMA and modified arginine. In these embodiments, antibodies specific for modified SDMA and antibodies specific for modified arginine are used to remove modified SDMA and modified arginine from a sample that has been reacted with an α-dicarbonyl compound, as described above. Once modified SDMA and modified arginine are removed from the sample, leaving ADMA, the ADMA is detected using any known method, including the above-mentioned methods. For example, antibodies specific for modified SDMA and antibodies specific for modified arginine are coupled to an insoluble support (e.g., immobilized), and, after reacting the biological sample with the α-dicarbonyl compound, the modified sample is contacted with the immobilized antibodies. After a suitable time, the modified sample is separated from the immobilized antibodies, and ADMA is detected in the sample. Antibodies can be immobilized on any of a variety of insoluble supports, including, but not limited to, beads, including magnetic beads, polystyrene beads; an affinity column matrix; a membrane; a plastic surface; and the like.

Antibodies

The present invention further provides antibodies that specifically bind ADMA. Antibodies that specifically bind ADMA do not detectably bind arginine, SDMA, modified arginine, or modified SDMA, or bind only at a background level. Antibodies specific for ADMA are useful for detecting ADMA in a sample that may comprise ADMA, SDMA, and arginine.

Alternatively, antibodies specific for modified SDMA and modified arginine are used together with antibodies directed against dimethylarginines (after modification of SDMA in the sample, only unmodified ADMA would be detected by these antibodies). Accordingly, the α-dicarbonyl modification can be used to enhance the specificity of any antibody binding to ADMA.

The present invention further provides antibodies that specifically bind modified SDMA, where the guanidino nitrogen residues are modified by reaction with an α-dicarbonyl compound, as described above. Antibodies that specifically bind modified SDMA do not detectably bind arginine, ADMA, or unmodified SDMA, or bind only at a background level.

The present invention further provides antibodies that specifically bind modified arginine, where the guanidino nitrogen residues are modified by reaction with an α-dicarbonyl compound, as described above.

In many embodiments, a subject antibody is isolated, e.g., is in an environment other than its naturally-occurring environment. Suitable antibodies are obtained by immunizing a host animal with ADMA, with modified SDMA, or with modified arginine, as appropriate. Suitable host animals include mouse, rat sheep, goat, hamster, rabbit, etc.

For preparation of polyclonal antibodies, the first step is immunization of the host animal with the antigen, i.e., ADMA, modified SDMA, or modified arginine, where the antigen will preferably be in substantially pure form, comprising less than about 1% contaminant. To increase the immune response of the host animal, the antigen is typically coupled to a carrier, and may be combined with an adjuvant, where suitable adjuvants include alum, dextran, sulfate, large polymeric anions, oil & water emulsions, e.g. Freund's adjuvant, Freund's complete adjuvant, and the like. The antigen is typically conjugated to a carrier molecule, e.g., a synthetic carrier molecule protein, a synthetic antigen, keyhole limpet hemocyanin, and the like. A variety of hosts may be immunized to produce the polyclonal antibodies. Such hosts include rabbits, guinea pigs, rodents, e.g. mice, rats, sheep, goats, and the like. The antigen is administered to the host, e.g., intradermally, or intraperitoneally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) J.B.C. 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also provided are "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516,637; 5,223,409; 5,658,727; 5,667,988; 5,498,538; 5,403,484; 5,571,698; and 5,625,033.

Also of interest in certain embodiments are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *Proc. Natl. Acad. Sci. USA*. 84:3439 and (1987) *J. Immunol*. 139: 3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods. Other methods for preparing chimeric antibodies are described in, e.g., U.S. Pat. No. 5,565,332.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) Mol. Cell. Bio. 3:280), Rous sarcoma virus LTR (Gorman et al. (1982) P.N.A.S. 79:6777), and moloney murine leukemia virus LTR (Grosschedl et al. (1985) Cell 41:885); native Ig promoters, etc.

In some embodiments, a subject antibody is detectably labeled. A detectable label is any composition detectable by spectroscopic, photochemical, biochemical, immunochemical, electrical, optical or chemical means. Detectable labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (a green fluorescent protein); a magnetic bead; colloidal gold or colored glass or plastic beads (e.g., polystyrene, polypropylene, latex, etc.) or other labels that can be detected by mass spectroscopy, NMR spectroscopy, or other analytical means known in the art.

A subject antibody can be labeled with a fluorescent protein as described in Matz et al., Nature Biotechnology (October 1999) 17:969-973; a green fluorescent protein (GFP), including a "humanized" GFP; a GFP from *Aequoria victoria* or fluorescent mutant thereof, e.g., as described in U.S. Pat. No. 6,066,476; 6,020,192; 5,985,577; 5,976,796; 5,968,750; 5,968,738; 5,958,713; 5,919,445; 5,874,304, the disclosures of which are herein incorporated by reference; a GFP from another species such as *Renilla reniformis, Renilla mulleri*, or *Ptilosarcus guernyi*, as described in, e.g., WO 99/49019 and Peelle et al. (2001) *J. Protein Chem*. 20:507-519; "humanized" recombinant GFP (hrGFP) (Stratagene); other fluorescent dyes, e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases.

In some embodiments, a subject antibody is labeled with an indirectly detectable label. An indirectly detectable label includes a member of a specific binding pair. Specific binding pairs include, but are not limited to, biotin-avidin, biotin-streptavidin, digoxin and antidigoxin and the like.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, e.g., in various dipstick assays, conjugated gold often appears pink, while various conjugated beads appear the color of the bead.

In some embodiments, a subject antibody is coupled (directly or through a linker) to an insoluble support. The antibody may be attached (coupled) to an insoluble support, including, but not limited to, a plastic surface (e.g., a polystyrene plate); a membrane (e.g., nitrocellulose, nylon, polyvinyl pyrollidone, polyester, polycarbonate, cellulose acetate, polyethersulfone, etc); a bead (e.g., a magnetic bead, a plastic bead); a colloidal particle; an affinity column matrix; and the like.

Detection using a subject antibody involves use of direct labels or indirect labels. Indirect labels include second antibodies specific for a subject antibody (e.g., specific for a heavy chain constant region of a subject antibody), wherein the second antibody is labeled as described above; and members of specific binding pairs, e.g., biotin-avidin, and the like. The biological sample may be brought into contact with an immobilized on a solid support or carrier, such as a membrane, beads, and the like, that is capable of immobilizing cells, cell particles, or soluble proteins. The support may then be washed with suitable buffers, followed by contacting with a detectably-labeled subject antibody. Detection methods are known in the art and will be chosen as appropriate to the signal emitted by the detectable label. Detection is generally accomplished in comparison to suitable controls, and to appropriate standards.

Kits

The present invention further provides kits for practicing the subject methods. A subject kit will include an α-dicarbonyl compound for modifying the guanidino nitrogen groups of SDMA and arginine; and an antibody. Suitable antibodies include those that bind specifically to ADMA; antibodies that specifically bind dimethylarginines (e.g., antibodies that bind both SDMA and ADMA); antibodies that specifically bind modified SDMA; antibodies that bind α-dicarbonyl forms of SDMA and α-dicarbonyl forms of L-arginine; and antibodies that specifically bind modified arginine. The subject kit components are typically present in a suitable storage medium, e.g., buffered solution, typically in a suitable container. A subject kit may further include membranes for carrying out an immunological assay, e.g., a test strip.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, compact disk (CD), digital versatile disk, etc., on which the information has been recorded. Yet another means that may be present is a website address which may be used via the internet to access the information at a removed site. Any convenient means may be present in the kits.

Utility

The subject methods and kits are useful for detecting ADMA in a biological sample. The subject methods are useful for determining a level of ADMA in a biological sample, and therefore are useful in diagnostic methods for various disorders, including methods for determining the risk of developing a disorder.

The subject methods are useful for diagnosing various disorders for which elevated ADMA levels are diagnostic, including, but not limited to, hypertension, hyperhomocysteinemia, hyperglycemia, hypercholesterolemia, insulin resistance, renal insufficiency, congestive heart failure, atherosclerosis, transplant arteriopathy, and endothelial dysfunction and the like. For example, an increase in the level of ADMA, compared to the level in a normal, healthy individual, indicates that the individual is at risk for vascular dysfunction or disease.

The subject methods are also useful for determining the extent, the severity, the progression, or stage, of a disorder for which an elevated ADMA level is diagnostic. A biological sample is taken at a single time point and the level of ADMA is compared to a chart of standard normal values for ADMA. The severity of the disorder is assessed by comparing the detected levels of ADMA in the biological sample with levels of ADMA in a standard curve, and associating the level with the severity of the disorder. The severity of the disorder may allow the selection of more efficacious therapies, for example a mild elevation of ADMA in a hypercholesterolemic subject may indicate that lifestyle changes are sufficient therapy, whereas a severe elevation of ADMA would indicate that drug therapy should be employed.

The subject methods are useful for monitoring progression of a disorder for which an elevated ADMA level is diagnostic. Determining ADMA levels at different times is used to monitor the progression of the disorder. A biological sample is taken from the individual and tested at a frequency of once per week, twice weekly, once per month, bimonthly, once every three months, once every four months, once every 6 months, or once a year, depending on various factors. In these embodiments, the level of ADMA in a test sample is compared to the level of ADMA in a previous sample(s). An increase in the level of ADMA in a test sample, compared to one or more previous test samples, indicates that the disease is increasing in severity. The rate of increase in the level of ADMA is an indication of the rate of progression of the disease. A reduction in ADMA may be seen with treatment (e.g., insulin-resistant subjects having elevated ADMA levels exhibit reduced ADMA levels following treatment with metformin).

The subject methods are also useful for determining the risk that an individual will develop a disorder for which an elevated ADMA level is diagnostic. An elevated ADMA level, compared to a control value for a normal healthy individual, may indicate that the individual is at risk for developing a disorder for which elevated ADMA levels are diagnostic. ADMA has been shown to be predictive of cardiovascular mortality in patients with coronary artery disease or renal insufficiency (Zoccali C, Bode-Boger S, Mallamaci F, Benedetto F, Tripepi G, Malatino L, Cataliotti A, Bellanuova I, Fermo I, Frolich J, Boger R. Plasma concentration of asymmetrical dimethylarginine and mortality in patients with end-stage renal disease: a prospective study. Lancet. 2001 Dec. 22-29;358(9299):2113-7. Valkonen V P, Paiva H, Salonen J T, Lakka T A, Lehtimaki T, Laakso J, Laaksonen R. Risk of acute coronary events and serum concentration of asymmetrical dimethylarginine. Lancet. 2001 Dec. 22-29;358(9299): 2127-8.) Additional tests may be recommended to determine whether an individual is developing a given disorder. In view of the test results, an appropriate treatment regimen may be recommended.

The subject methods are also useful for determining the response of an individual to treatment for a disorder for which an elevated ADMA level is diagnostic. Measurements of ADMA levels are used to determine whether a patient is responding to treatment. ADMA levels are measured before and after a treatment to determine if the treatment is efficacious. ADMA levels are also determined during the course of the treatment, to determine whether the treatment slows the progression of the disease, and to what extent the treatment slows the progression of the disease.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Method for Modifying SDMA and Arginine

There are two isoforms of dimethylarginine—asymmetric (SDMA) and symmetric (ADMA), depending on how the methyl groups are distributed on the guanidino function group of arginine. Any detection method for ADMA needs to be able to distinguish among ADMA, SDMA, and arginine, which are structurally very similar. Some HPLC system can achieve the resolution; however, it suffers from the drawbacks mentioned above. Available antibodies against dimethylarginine, though improving efficiency and sensitivity, indiscriminately bind to both ADMA and SDMA (e.g., ab413, Abcam, Cambridge Science Park, UK). The following approach utilizes a chemical reaction that specifically modifies SDMA, but not ADMA. SDMA, but not ADMA, will react with α-dicarbonyl compounds, leaving the modified SDMA to sufficiently differ from ADMA such that an antibody directed against dimethylarginines can then be used to selectively detect ADMA. This method also enhances the selectivity of antibodies or engineered molecules that preferentially (but not selectively) detect ADMA.

Figure 2:
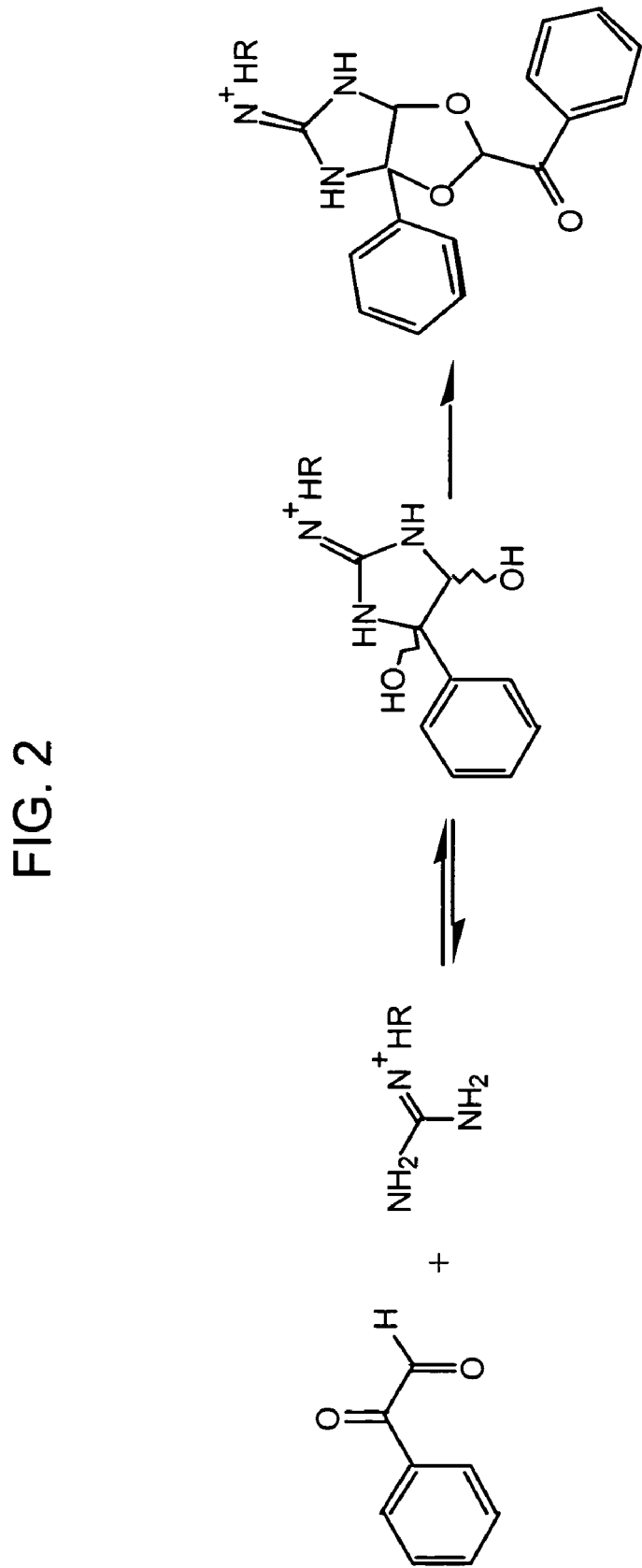
FIG. 2 depicts the reaction of phenylglyoxal with an arginine residue.

A large number of α-dicarbonyl compounds (dialdehydes, ketoaldehydes and diketones) have been used in the past four decades to modify arginine residue in proteins. Before site-specific mutation became available, such modification indicates whether an arginine residue is part of an enzyme's active site. Phenylglyoxal (FIG. 1) is an α-dicarbonyl compound still in use today for active site determination. Under mild conditions, phenylglyoxal reacts with the arginine residue. Acting as nucleophiles, the guanidino nitrogens from arginine attack the carbonyl carbons, forming a five-member ring structure. The unstable dialcohol intermediate then reacts with another phenylglyoxal, giving rise to a product that contains two phenylglyoxal moieties per guanidino group (FIG. 2).

This product is relatively stable at acidic pH's, but at pH>10, the reaction was observed to be reversible. Typically, phenylglyoxal is dissolved in water and the pH is adjusted to 9.0 with 1M NaOH. A solution containing phenylglyoxal is then added to the sample in such a way that the stock solution is diluted 10-fold. The reaction proceeds in the dark at room temperature for 60-180 minutes (Reference: Tawfik D S, Walter J M, Modification of arginine side chains with p-hydroxyphenylglyoxal, *The Proteins Protocol Handbook* 2002, $2^{nd}$ edition, Humana Press Inc.)

In addition to reacting with the guanidino amine of arginine, phenylglyoxal has been reported to react with the α-amino group of the peptides to give α-keto acyl peptides. In the context of free amino acid, this observation indicates that phenylglyoxal will react with all α-amino group of all amino acid. To ensure that phenylglyoxal only reacts with the guanidino nitrogen, we can protect the α-amino group with a conventional labeling dye such as fuoro-nitro-benzoxadiazole (NBD-F). Many labeling dye molecules are conjugated to the amino acid or proteins by binding to the α-amino group.

Figure 3:
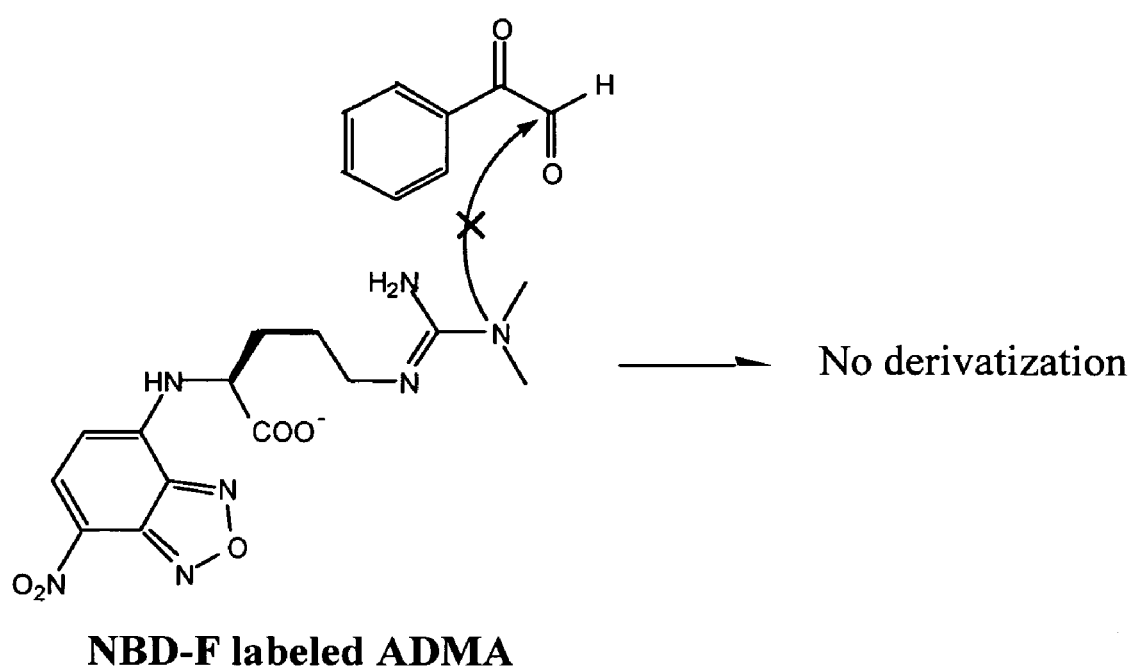
FIG. 3 depicts fluoro-nitro-benzoxadiazole labeled ADMA.

After the α-amino group of SDMA and ADMA are protected by reacting with NBD-F, phenylglyoxal would be added to the mixture. Since the guanidino nitrogens on SDMA each take up one methyl group, they both still possess a hydrogen free to participate in nucleophilic reaction. ADMA, on the other hand, has both methyl groups occupying the same guanidino nitrogen, disabling that nitrogen from further reaction (FIG. 3).

Figure 4:
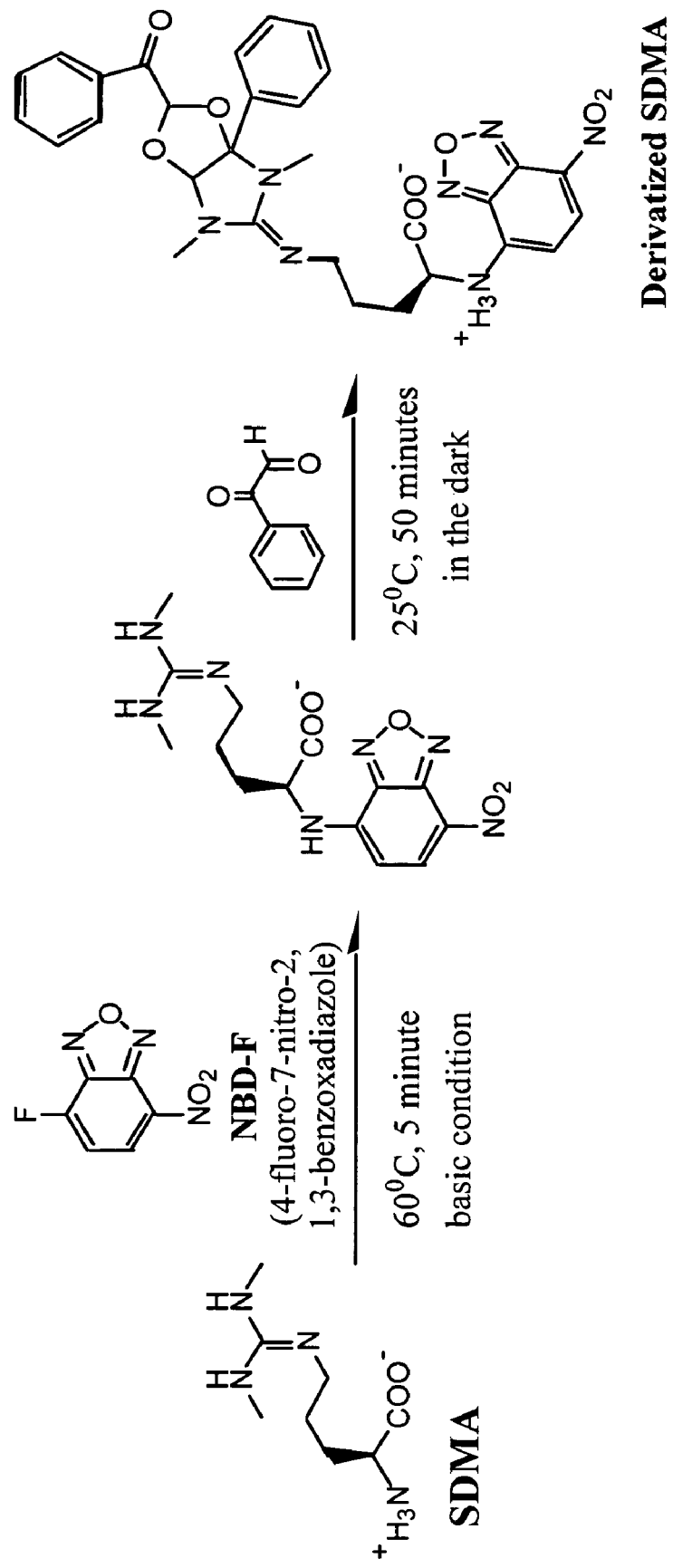
FIG. 4 depicts the reaction of SDMA with phenylglyoxal.

Participation of both guanidino nitrogens in the reaction with phenylglyoxal is crucial for the ring formation, and hence stability, of the final product. Thus, SDMA, but not ADMA, would react with phenylglyoxal, via the reaction outlined in FIG. 4.

According to the above scheme, phenylglyoxal would react with both SDMA and arginine. An antibody against dimethylarginines could be used to specifically detect ADMA, by first reacting the samples with phenylglyoxal, which modifies SDMA, but not ADMA.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of detecting asymmetric dimethylarginine (ADMA) in a sample comprising ADMA and at least one of symmetric dimethylarginine (SDMA) and arginine, the method comprising the steps of:
   a) contacting the sample with an agent that protects the α-amino group of ADMA and the α-amino group of the at least one of SDMA and arginine, generating a sample comprising ADMA having a protected α-amino group and at least one of SDMA and arginine having a protected α-amino group;
   b) contacting the sample generated in step (a) with an α-dicarbonyl compound, wherein said α-dicarbonyl compound modifies the guanidino nitrogens of SDMA and the guanidino nitrogens of arginine, producing modified SDMA and modified arginine, wherein said modified SDMA and said modified arginine are distinguishable from ADMA; and
   c) detecting ADMA in the sample generated in step (b).

2. The method of claim 1, wherein said α-dicarbonyl compound is phenylglyoxal.

3. The method of claim 1, wherein the agent that protects the α-amino group is a dye that provides a detectable signal.

4. The method of claim 3, wherein the dye is a fluorophore.

5. The method of claim 4, wherein the fluorophore is fluoro-7-nitrobenzofurazan.

6. The method of claim 1, wherein said detecting step comprises contacting the sample with an antibody that binds specifically to ADMA, to SDMA, or to both ADMA and SDMA, wherein said antibody does not bind to the modified SDMA.

7. The method of claim 6, wherein the antibody is detectably labeled.

8. The method of claim 1, wherein said detecting step comprises contacting the sample with an antibody that binds specifically to the α-amino group-modified ADMA.

9. The method of claim 8, further comprising detecting one or more of modified SDMA and modified arginine, wherein said detection of one or more of modified SDMA and modified arginine comprises contacting the sample with an antibody that binds specifically to one or more of modified SDMA and modified arginine.

10. The method of claim 1, wherein said ADMA is detected by high performance liquid chromatography.

11. The method of claim 1, wherein said ADMA is detected by capillary electrophoresis.

12. The method of claim 1, wherein the α-dicarbonyl compound is selected from biacetyl, pyruvic acid, glyoxal, methyglyoxal, deoxyosones, 3-deoxyosones, malondialdehyde, 2-oxopropanal, phenylglyoxal, 2,3-butanedione, and 1,2-cyclohexanedione.

13. The method of claim 1, wherein the sample is a biological sample.

14. The method of claim 13, wherein the biological sample is serum or plasma.

15. The method of claim 13, wherein the biological sample is subjected to solid phase extraction before step (a) to clean up the sample.

16. The method of claim 1, wherein the agent that protects the α-amino group is ortho-phthaldialdehyde.

* * * * *

UNITED STATES PATENT AND TRADEMARK OFFICE
CERTIFICATE OF CORRECTION

| | | |
|---|---|---|
| PATENT NO. | : 7,611,844 B2 | Page 1 of 1 |
| APPLICATION NO. | : 10/713674 | |
| DATED | : November 3, 2009 | |
| INVENTOR(S) | : Ken Y. Lin | |

It is certified that error appears in the above-identified patent and that said Letters Patent is hereby corrected as shown below:

Please replace on column 1, line 14, with the following revised statement:

STATEMENT REGARDING FEDERALLY SPONSORED RESEARCH

-- This invention was made with Government support under contract no. HL063685 awarded by the National Institutes of Health. The Government has certain rights in this invention. --

Signed and Sealed this

Eleventh Day of May, 2010

David J. Kappos
*Director of the United States Patent and Trademark Office*